United States Patent [19]
Persico et al.

[11] Patent Number: 5,919,899
[45] Date of Patent: Jul. 6, 1999

[54] HUMAN PROTEIN WITH ANGIOGENESIS REGULATIVE PROPERTIES

[75] Inventors: Maria Persico; Domenico Maglione, both of Naples, Italy

[73] Assignee: Consiglio Nazionale Delle Ricerche, Rome, Italy

[21] Appl. No.: 08/039,297

[22] PCT Filed: Sep. 26, 1991

[86] PCT No.: PCT/IT91/00079

§ 371 Date: Apr. 19, 1993

§ 102(e) Date: Apr. 19, 1993

[87] PCT Pub. No.: WO92/06194

PCT Pub. Date: Apr. 16, 1992

[30] Foreign Application Priority Data

Sep. 27, 1990 [IT] Italy ..................................... 48315/90

[51] Int. Cl.$^6$ ................................................. C07K 14/435
[52] U.S. Cl. .......................... 530/350; 435/69.1; 530/399
[58] Field of Search ..................................... 530/350, 399; 435/69.1, 240.1, 252.3, 254.11, 320.1; 536/23.1, 23.5

[56] References Cited

PUBLICATIONS

Abstract—"Keystone Symposia on Molecular & Cellular Biology", *Journal of Cellular Biochemistry*, 20th Annual Meetings, Supplement 15F, 1991, Apr. 1–Apr. 7, 1991, (Abstract No. CF 316).

Keck et al., "Vascular Permeability Factor, an Endothelial Cell Mitogen Related to PDGF", *Science*, vol. 246, 1989, pp. 1309–1312.

Ishikawa et al., "Identification of Angiogenic Activity and the Cloning and Expression of Platelet–Derived Endothelial Cell Growth Factor", *Nature*, vol. 338, Apr. 13, 1989, pp. 557–562.

Maglione et al, PNAS, v. 88, p. 9267, 1992.

*Primary Examiner*—Sally P. Teng
*Attorney, Agent, or Firm*—Smith, Gambrell & Russell, LLP; Beveridge, DeGrandi, Weilacher & Young; Intellectual Property Group

[57] ABSTRACT

Disclosed are an isolated and purified protein acting as an angiogenic factor and nucleotide sequences encoding for such a protein, vectors containing such sequences and cells transformed by such vectors.

1 Claim, 3 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1645 base pairs
      (B) TYPE: nucleic acid
      (C) STRANDEDNESS: single
      (D) TOPOLOGY: linear (xi) SEQUENCE DESCRIPTION: SEQ ID NO:1:

```
GGGATTCGGG CCGCCCAGCT ACGGGAGGAC CTGGAGTGGC ACTGGGCGCC CGACGGACCA        60

TCCCCGGGAC CCGCCTGCCC CTCGGCGCCC CGCCCCGCCG GGCCGCTCCC CGTCGGGTTC       120

CCCAGCCACA GCCTTACCTA CGGGCTCCTG ACTCCGCAAG GCTTCCAGAA GATGCTCGAA       180

CCACCGGCCG GGGCCTCGGG GCAGCAGTGA GGGAGGCGTC CAGCCCCCCA CTCAGCTCTT       240

CTCCTCCTGT GCCAGGGGCT CCCCGGGGGA TGAGCATGGT GGTTTTCCCT CGGAGCCCCC       300

TGGCTCGGGA CGTCTGAGAA GATGCCGGTC ATGAGGCTGT TCCCTTGCTT CCTGCAGCTC       360

CTGGCCGGGC TGGCGCTGCC TGCTGTGCCC CCCCAGCAGT GGGCCTTGTC TGCTGGGAAC       420

GGCTCGTCAG AGGTGGAAGT GGTACCCTTC CAGGAAGTGT GGGGCCGCAG CTACTGCCGG       480

GCGCTGGAGA GGCTGGTGGA CGTCGTGTCC GAGTACCCCA GCGAGGTGGA GCACATGTTC       540

AGCCCATCCT GTGTCTCCCT GCTGCGCTGC ACCGGCTGCT GCGGCGATGA GAATCTGCAC       600

TGTGTGCCGG TGGAGACGGC CAATGTCACC ATGCAGCTCC TAAAGATCCG TTCTGGGGAC       660

CGGCCCTCCT ACGTGGAGCT GACGTTCTCT CAGCACGTTC GCTGCGAATG CCGGCCTCTG       720

CGGGAGAAGA TGAAGCCGGA AAGGTGCGGC GATGCTGTTC CCCGGAGGTA ACCCACCCCT       780

TGGAGGAGAG AGACCCCGCA CCCGGCTCGT GTATTTATTA CCGTCACACT CTTCAGTGAC       840

TCCTGCTGGT ACCTGCCCTC TATTTATTAG CCAACTGTTT CCCTGCTGAA TGCCTCGCTC       900

CCTTCAAGAC GAGGGGCAGG GAAGGACAGG ACCCTCAGGA ATTCAGTGCC TTCAACAACG       960

TGAGAGAAAG AGAGAAGCCA GCCACAGACC CCTGGGAGCT TCCGCTTTGA AAGAAGCAAG      1020
```

```
ACACGTGGCC TCGTGAGGGG CAAGCTAGGC CCCAGAGGCC CTGGAGGTCT CCAGGGGCCT    1080

GCAGAAGGAA AGAAGGGGGC CCTGCTACCT GTTCTTGGGC CTCAGGCTCT GCACAGACAA    1140

GCAGCCCTTG CTTTCGGAGC TCCTGTCCAA AGTAGGGATG CGGATCCTGC TGGGGCCGCC    1200

ACGGCCTGGT GGTGGGAAGG CCGGCAGCGG GCGGAGGGGA TCCAGCCACT TCCCCCTCTT    1260

CTTCTGAAGA TCAGAACATT CAGCTCTGGA GAACAGTGGT TGCCTGGGGG CTTTTGCCAC    1320

TCCTTGTCCC CCGTGATCTC CCCTCACACT TTGCCATTTG CTTGTACTGG GACATTGTTC    1380

TTTCCGGCCG AGGTGCCACC ACCCTGCCCC CACTAAGAGA CACATACAGA GTGGGCCCCG    1440

GGCTGGAGAA AGAGCTGCCT GGATGAGAAA CAGCTCAGCC AGTGGGGATG AGGTCACCAG    1500

GGGAGGAGCC TGTGCGTCCC AGCTGAAGGC AGTGGCAGGG GAGCAGGTTC CCCAAGGGCC    1560

CTGGCACCCC CACAAGCTGT CCCTGCAGGG CCATCTGACT GCCAAGCCAG ATTCTCTTGA    1620

ATAAAGTATT CTAGTGTGGA AACGC                                          1645

(2) INFORMATION FOR SEQ ID NO:2:

(i) SEQUENCE CHARACTERISTICS:
        (A) LENGTH: 149 amino acids
        (B) TYPE: amino acid
        (C) STRANDEDNESS: single
        (D) TOPOLOGY: unknown (xi) SEQUENCE DESCRIPTION: SEQ ID NO:2:

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Cys Gly Asp
    130                 135                 140

Ala Val Pro Arg Arg
145

(2) INFORMATION FOR SEQ ID NO:3:

(i) SEQUENCE CHARACTERISTICS:
        (A) LENGTH: 826 base pairs
        (B) TYPE: nucleic acid
        (C) STRANDEDNESS: single
        (D) TOPOLOGY: unknown (xi) SEQUENCE DESCRIPTION: SEQ ID NO:3:

GTAAGTGGTT TGGCTGGGGC TCGGGGCTAT TCTATTCTCG GGCCTGCCAG CCTCTGTCCT     60

AGCATGGGGT TCCCCAGCCA CCTTGTCCTG ACGCTTGGCT TATTGCAGGA GGAGACCCAA    120

GGGCAGGGGG AAGAGGAGGA GAGAGAAGCA GAGACCCACA GACTGCCACC TGTGAGTGCG    180
```

```
CGGGGTCCCA GGGATGGCGA GGAGGCTGGG CCCGAGGGGA GCCCCGCCTT GCCGCGAGGG      240

TTAGGTTGGG GAGGGGGAGA GGCAGGACTG AGGCGAGTCT TGGGGGCAGA ACAGGGANCT      300

GCACCTCCTC AAGACTCTAG GGCCCAGGAA GCATCAGTGG ACCTTGGTTT TTATCCCGGC      360

TTAGCCTAGG TTTCCATTGA CCTTCAACAA ATCATTTCAC CTTTGTCAGC CTAGCTTTTC      420

TCTGTGTAGA ATGAGGGGCA GGAGGTCCAG CAAACATTCA GTCACTCTAC AAACATTTAC      480

TGAGCACTTA CTGTGTGTCA GGTACATCTG TGAGCAAACA AACAGGATTC CTGCACATTA      540

GTGTTTACCT TTTAGTGATT AAAAGTCTGT CATCAGCTGA GACGTTATCT GGGGCCACTT      600

CCTAGTAGCC CGGGGAACAT GTGCCCTCNC ACTGTCTCCC AGGAGTATTT TGCCTGTGG       660

GTCCCCTTGC TGCTTCTAAC CCACTTCGTA CCTTGTGGGC AGCAGAATGG AGCCCCAGGC      720

CTGAGTGTGG CTGGGAGAGA AGGATGAGAG GAGGGAAAAC CCAAATCTGT GAGAGTAAAT      780

AGAAAAAATA AAATATTTCA CGTGCACAGT CAATCAGTCA GTGAAG                    826
```

(2) INFORMATION FOR SEQ ID NO:4:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:4:

```
AGGAGACCCA AGGGCAGGGG GAAGAGGAGG AGAGAGAAGC AGAGACCCAC AGACTGCCAC      60

CTG                                                                    63
```

(2) INFORMATION FOR SEQ ID NO:5:

(i) SEQUENCE CHARACTERISTICS:
        (A) LENGTH: 21 amino acids
        (B) TYPE: amino acid
        (C) STRANDEDNESS: single
        (D) TOPOLOGY: unknown (xi) SEQUENCE DESCRIPTION: SEQ ID NO:5:

```
Arg Arg Pro Lys Gly Arg Gly Lys Arg Arg Glu Lys Gln Arg Pro
1               5                   10                  15

Thr Asp Cys His Leu
            20
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

```
TCCTCCAAGG GGATCCTGGG TTAC                                             24
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

```
GCAAGGGGTA TACTCGTCTG TTCC                                             24
```

(2) INFORMATION FOR SEQ ID NO:8:

(i) SEQUENCE CHARACTERISTICS:
        (A) LENGTH: 170
        (B) TYPE: amino acid
        (C) STRANDEDNESS: single
        (D) TOPOLOGY: unknown (xi) SEQUENCE DESCRIPTION: SEQ ID NO:8:

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Arg Arg Pro
130                 135                 140

Lys Gly Arg Gly Lys Arg Arg Arg Glu Lys Gln Arg Pro Thr Asp Cys
145                 150                 155                 160

His Leu Cys Gly Asp Ala Val Pro Arg Arg
                165                 170
```

HUMAN PROTEIN WITH ANGIOGENESIS REGULATIVE PROPERTIES

INTRODUCTION AND BACKGROUND

This invention relates to nucleotide sequences coding for a human protein having angiogenesis regulative properties.

More particularly, this invention relates to the isolation and to the molecular characterization of a gene coding for a new protein having the properties of an angiogenic factor which regulates in vivo the formation and/or the regeneration of the vertebrate blood vessel system, and it also relates to the protein itself. Moreover, this invention also refers to vectors containing such sequence or parts thereof, to prokaryotic and eukaryotic cells transformed with such vectors, and to the employment of such vectors and of such cells for the production of the protein and of corresponding polyclonal and/or monoclonal antibodies as well.

It is well known that growth factors are polypeptides, synthesized and secreted by mammalian cells, capable of acting not only on the proliferation, but also on the differentiation and morphogenesis of target cells. Indeed, it has been shown that some growth factors exert their action by regulating mechanisms such as chemotaxis, activation of inflammatory system cells and repairing of tissues (Whitman, M. and Melton, D. A., 1989, Annual Rev. Cell Biol., 5. 93–117).

Because of the similar phenotype between cultured growth factors stimulated and retrovirus transformed cells, it has been suggested that common mechanisms control such phenomena. Indeed, the interaction between a growth factor and its own specific receptor indirectly activates gene activity regulative proteins, through intermediate reactions involving different protein-kinases. Many of the components of this metabolic chain have been identified as the cellular analogs of viral oncogenes, suggesting how oncoviruses could interfere with normal cellular processes.

Many growth factors have been identified up to the present time, the corresponding genes have been cloned, and such factors have been divided into groups, on the basis of similar activities and/or of sequence homologies; among them there is the family of angiogenic factors.

Angiogenesis, or the formation of vessels of the vascular system, is a complex process occuring during embroyogenesis, wound healing and organ regeneration. Moreover, some pathologies like the growth of solid tumors, some retinopathies and rheumatoid arthritis induce an aberrant angiogenesis (Risau W., 1990, Progress in Growth Factor Research, 2, 71–79).

Angiogenesis in vivo is a multi-step process, two of them being represented by the migration and the proliferation of endothelial cells devoted to the formation of vessels.

In the most recent years, many angiogenic factors have been identified, and the corresponding genes cloned. Among them: angiogenin, subject-matter of the patent application PCT no.8701372; the platelet-derived endothelial growth factor PD-ECGF (Ishigawa et al., 1989, Nature, 338, 557); the human vascular permeability factor, VPF (Keck et al., 1989, Science 246, 1309), which was cloned also in the mouse with the denomination of vascular endothelial growth factor, VEGF (Leung et al., 1989, Science, 246, 1306); the growth factor for fibroblasts, i.e., the acid factor, a-FGF, and the basis factor, b-FGF, the transforming growth factors alpha, TGF-α, and beta, TGF-β(Folkman and Klagsburn, 1987, Science, 235, 442).

Angiogenic factors have been divided into two groups, according to their way of action: either directly on the vascular endothelial cells, by stimulating motility or mitosis, or indirectly on cells producing growth factor acting on endothelial cells.

In vitro analysis have put into evidence that angiogenic factors exert different effects on the motility and on the proliferation of endothelial cells. Indeed, some of them stimulate just one of the two events, other ones stimulate both events, whereas others seem to be ineffective in vitro, and, lastly, other ones show even an inhibiting activity of the endothelial cellular proliferation. Such data point out that the regulation of angiogenesis is a complex process mediated by different components, many of which have not been identified as yet.

Accordingly it is evident that there is the need for identifying and isolating new angiogenic factors capable of stimulating the migration and differentiation of endothelial cells, to be utilized both in the diagnostic field, as tumoral markers and for inflammatory diseases, and in the therapeutical field, for topic or internal use, for instance in the treatment of wounds, of tissues after a surgical operation, of transplantation, of burns, ulcers, etc.. Such factors can be employed successfully also in vitro, as growth-stimulating of cell cultures.

Moreover, DNA recombinant techniques allow such factors to be produced in suitable amounts, in short times and at remarkably low costs.

Indeed, there is an increasing need for identifying new specific tumoral markers because of uncertainties in tumor diagnosis. Moreover, recent methods for producing hybrid proteins (Fitzgerald D. and Pastan I., 1989, J. Natl. Cancer Inst. 81, 1455–1463) and/or conjugate antibodies (Pearson, J. W. et al., 1989 Cancer Res. 49, 3562–3567) with toxic molecules, are giving promising results in the field of tumoral serotherapy, with an increasingly growing demand for new factors to test. Finally, many of angiogenic factor genes have been cloned starting from tumoral cells, whereas a better applicability in the therapeutic field of genes coming from non-neoplastic material is evident.

SUMMARY OF THE INVENTION

Accordingly, this invention provides nucleotide sequences coding for a protein having a regulative activity of angiogenesis, said sequences being obtained from non-neoplastic tissue; vectors containing said sequences; cells transformed by said vectors and producing protein having biologic and/or immunologic activities of a new angiogenic factor, as well as the protein itself, to be employed in diagnostic and theraupetic fields.

This invention also provides a procedure for obtaining the protein, or parts thereof, by recombinant techniques, as well as its use as an antigen for the production of the corresponding polyclonal or monoclonal antibodies.

Indeed, molecular probes comprising sequences coding for the angiogenic factor subject-matter of the present invention can be employed as markers in the diagnosis of pathologies related to the aberrant production thereof, as the case of some tumoral pathologies for other angiogenic factors.

Moreover, the protein which is another subject-matter of this invention can be employed in the treatment of inflammatory diseases, in the treatment of wounds, of tissues after surgical operations, of transplantation, of burns of ulcers and so on. Such factor can also be employed in vitro successfully, as growth stimulating of cell cultures.

Finally, DNA recombinant techniques employed in the present invention allow to produce the molecular probes and proteins described above in suitable amounts, in short times and at remarkably reduced costs.

The nucleotide and amino acids chains of this invention can be employed for diagnostic tests and for theraupetic purposes, both as directly derived from host cells and as after suitable modifications, for obtaining a better product for pharmaceutical compositions.

Accordingly, the object of this invention consists in nucleotide sequences coding for a protein, named PlGF, with immunogenic and/or biologic properties of an angiogenesis regulative factor, having the amino acids sequence of SEQ ID NO:2.

As another embodiment of the invention, the PlGF amino acid sequence (SEQ ID NO:8) derives from alternative splicings of the primary transcript, preferably at the nucleotide sequence shown in SEQ ID NO:4, most preferably giving rise to an amino acid insertion of 21 amino acids, whose sequence is shown in SEQ ID NO: 5, at position 141–142 of the amino acid sequence shown in SEQ ID NO:2.

An object of this invention also consists in nucleotide sequences coding for the PlGF protein, lacking and/or substituted in one or more amino acids, preferably deleted from the amino acid 1 to the amino acid 31 of SEQ ID NO:2; the present invention also provides nucleotide sequences which are allelic derivatives of the sequence coding for SEQ ID NO:1; as well as nucleotide sequences that are complementary to those coding for SEQ ID NO:1.

Again according to the present invention the nucleotide sequence can be covalently bounded to a nucleotide sequence which can be translated into amino acid sequence by employing the same reading frame of the gene coding for PlGF, which preferably does not interfere with the angiogenesis regulative activity of PlGF, and which more preferably codes for a protein portion having toxic activity.

Accordingly, the object of this invention also consists in the nucleotide sequence of SEQ ID NO:1, even though the same is lacking and/or substituted in one or more nucleotides, coding at its coding part for the protein PlGF, as in SEQ ID NO:2.

The present invention also provides nucleotide sequences hybridizing with SEQ ID NO: 1, or parts thereof; nucleotide sequences obtained both through natural and synthetic or semisynthetic methods, by substitution, deletion, insertion and inversion mutations, either concerning single bases or multiple bases, of sequence described in SEQ ID NO:1, or parts thereof; and nucleotide sequences comprising sequences coding for a protein having immunogenic and/or biologic properties similar to those exhibited by the protein PlGF or parts thereof.

A further aspect of this invention relates to the protein PlGF having the sequence disclosed in SEQ ID NO:2, or parts thereof, obtained either by means of recombinant DNA techniques or isolated from biologic tissues. Said protein, or parts thereof which are immunologically active, can be employed as antigenes for producing polyclonal and/or monoclonal antibodies.

The present invention also provides cloning and/or expression vectors, both prokaryotic and eukaryotic, comprising the nucleotide sequences subject-matter of the invention, sequences promoting transcription located upstream and, in general, a selective marker. Preferably, sequences promoting transcription in an inducible manner, can also be present and enhancers, polyadenylation signals and so on, as well.

Again an object of the present invention consists in prokaryotic and eukaryotic cells transformed by said vectors to be employed for producing the PlGF protein or parts thereof.

BRIEF DESCRIPTION OF THE DRAWINGS

Just for illustrative and not for limitative purposes the present invention will be described in the following examples. In what follows reference will be made to the enclosed Figures wherein.

DETAILED DESCRIPTION OF THE INVENTION

EXAMPLE 1

Isolation of the cDNA coding for a new angiogenic factor (SEQ ID NO:7)

A first cDNA fragment, named sub 32, was isolated from a clone of a cDNA library from human placenta, in the λ GT11 vector, according to conventional procedures and employed also in other laboratories (Wataneb et al., J. Biol. Chem. 246, 12611–19, 1989).

Figure 1:
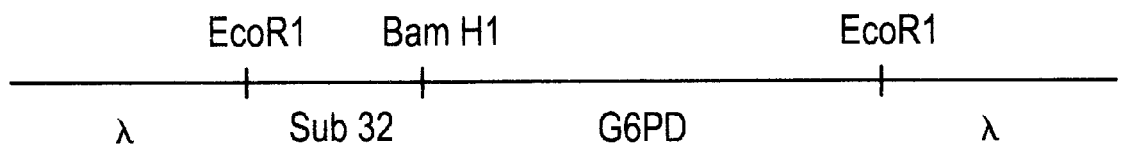
FIG. 1 represents the restriction map of the recombinant λ GT11 phage, comprising the sub 32 fragment.
Figure 3:
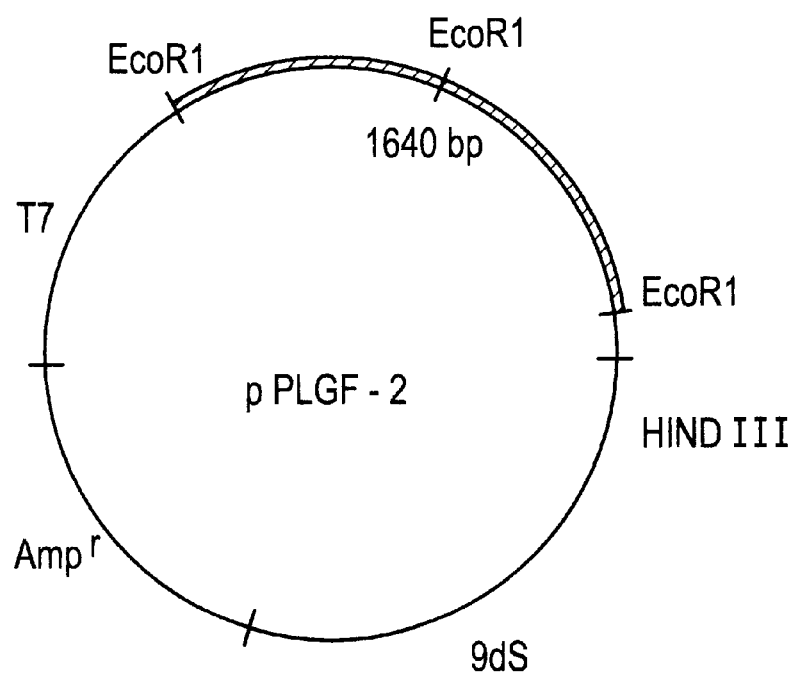
FIG. 3 represents the restriction map of the plasmid pPlGF-2.
Figure 2:
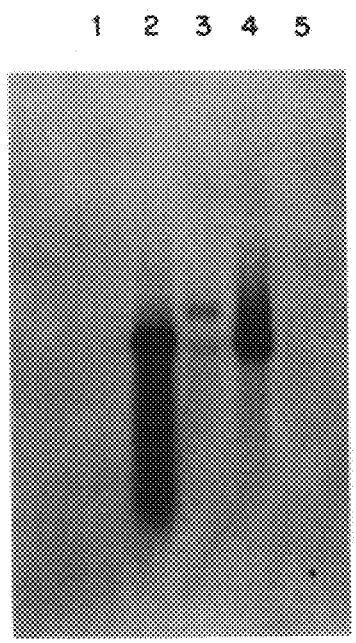
FIG. 2 represents a "Northern blot" experiment employing the sub 32 cDNA fragment.

Briefly, RNA was extracted through lysis with guanidine thiocyanate and centrifuging on a discontinuous gradient of caesium (Sambrook J., Fritsch E. F., Maniatis T., Molecular Cloning - A Laboratory Manual. Second edition. Vol. 1, 7.19. Cold Spring Harbor Lab. Press). The poly A- RNA was purified through chromatography on oligo-dT cellulose (ibid. 7.26). The cDNA synthesis and the cloning of the λ GT11 phage vector (Stratagene, La Jolla Calif., USA) in the Eco R1 restriction site was carried out following the protocol described ibid. 8.54–8.79. A clone, whose map is shown in FIG. 1, was identified because of comprising also a sequence of 2600 nucleotides capable of hybridizing, in 5×SEC at 65° C. according to the hybridization procedure on filters described ibid. 8.46, with a sequence coding for the cDNA of the glucose-6-phosphate dehydrogenase enzyme (G6PD) (Persico, M. et al., 1986, Nucl. Acid Res., 14, 2511). A fragment of 240 nucleotides was also isolated from this recombinant phage after digestion with Eco R1 and Sam H1, and the fragment was called sub 32. Said fragment, after labelling with 32P by means of the "nick translation" procedure disclosed ibid. 10.6–10.8 was employed for:

a) analyzing RNAs extracted from different tissues or cell lines, by "Northern blot" procedure as described in ibid. 7.37. The results shown in FIG. 2 show that the sub 32 fragment detects specific mRNA in the placenta (line 2), in HEPG2 hepatoma cells, ATCC N. HBB065 (line 3), in JEG human choriocarcinoma cells, ATCC N. HTB36 (line 4) and, at lower concentration, in Hela S3 cells, ATCC N. CCL2.2 (line 5), but not in HL60 cells, ATCC N. CCL240 (line 1);

b) screening a cDNA library from JEG human choriocarcinoma JEG, ATCC N. HTB36, according to the procedures described for the cDNA library from human placenta, in the λ GT10 vector (Stratagene, La Jolla Calif., USA), in the Eco R1 site. Two clones were isolated, digested with Eco R1 and subcloned in the pUC 18 vector (Stratagene, La Jolla, Calif., USA) and the sequence determined by Sanger's method (ibid. 13.6–13.10). The sequence revealed the fragmnents overlapped partially one another, but did not comprise the whole sequence coding for the corresponding mRNA. Hence, the isolated fragments were employed for a second screening, employing the same techniques. The library employed was the cDNA library from human placenta, from which the initial sub 32 fragment came from. Then two clones were isolated, their DNA was digested with Eco R1, the resulting inserts were subcloned in the pGEM 1 vector (Promega Corporation, Madison Wis., USA) and their sequence was determined by Sanger's method. The two DNA fragments obtained after digestion with Eco R1 were religated together through T4-ligase and cloned in the same pGEM 1 vector in the Eco R1 site, to obtain the whole cDNA sequence corresponding to the mRNA present in the placenta, in a single plasmid, called pPIGF-2 (ATCC Dep. No. 40892), whose map is shown in FIG. 3.

In order to confirm that the resulting fragment covers the whole coding sequence, the sequence was compared with the sequence of a genoma fragment obtained after hybridization of the same fragment with a genomic library from human fibroblasts WI38 (No. 944201 Stratagene, La Jolla, Calif., USA) in the λ Fix vector.

The cDNA sequence was identified according to Sangor's method (ibid. 13.3—13.10) and revealed:

a) a 5' end untranslated region of 321 nucleotides comprising a sequence capable of forming a stem-loop secondary structure, indicative of a translation regulative signal;

b) a sequence of 447 nucleotides with an open reading frame coding for a protein of 149 amino acids, comprising a hydrophobic sequence of 32 amino acids at the NH2-terminal, indicative of the signal peptide of secreted proteins;

c) a 3' end untranslated region of 877 nucleotides comprising a polyadenylation site.

The amino acid sequence, deduced by the cDNA sequence, was inserted into the European Molecular Biology Laboratory (EMBL) Data Bank, showing no protein with the same sequence. A 50% homology, limited to a 120 amino acid region, was shown with the vascular permeability factor VPF (Keck et al., 1989, Science 246, 1309), a powerful angiogenic factor, thus suggesting that the new protein PIGF can have by itself an angiogenesis-regulating activity.

EXAMPLE 2
Screening of a cDNA library from JEG-3 cells with pPLGF and structure of PIGF-gene A cDNA library, obtained from JEG-3 cell mRNA, was screened with the PIGF probe. Six recombinant phages were isolated. The sequences of two of them revealed they have a lenght of 510 bp, generating a 170 amino acid protein. The sequence resulted to be identical to the cDNA isolated from placenta, but an insertion of 63 bp, generating a 21 amino acid insertion into the protein, at position 141–142. Interestingly, the new sequence contains 10 amino acids (Arg and Lys) over 21.

EXAMPLE 3
Genomic mapping and cloning of the PIGF gene

The gene coding for the protein PIGF was mapped on the chromosome 14 through "Southern blot" analysis, by employing DNA from different hybrid cellular lines, each containing different human chromosomes (not shown).

The structure and part of the nucleotide sequence of the PIGF gene was determined from a human genomic library. The gene is divided into six exons and five intervening sequences generating, through splicing, the transcript coding for the 149 aa. protein of SEQ ID NO: 2. In choriocarcinoma cells (JEG-3) the primary transcript is alternatively spliced at the fifth intron to generate a transcript coding for the 170 aa. (see SEQ ID NO:2 SEQ ID NO:5). Another alternative splicing involving the sequence from 174 to 828 of SEQ ID NO:3 of the fifth intron, gives rise to an higher molecular weigth PIGF protein. In fact two proteins are immunoprecipitated from JEG-3 conditioned medium, with antibodies anti PIGF.

EXAMPLE 4
Subcloning of PIGF cDNA in a prokaryotic expression vector

Figure 4:
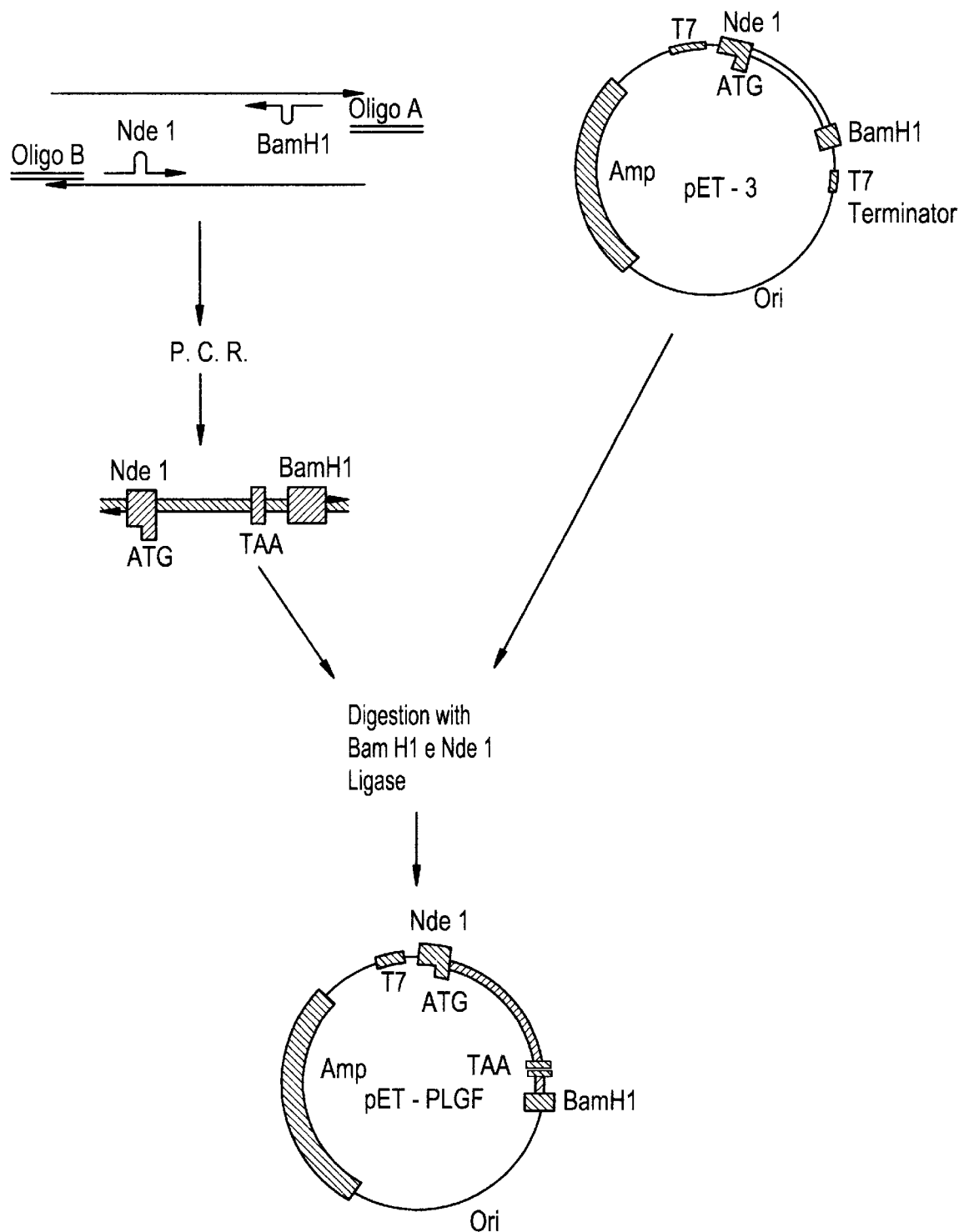
FIG. 4 represents an exemplificative scheme of subcloning of a fragment coding for a portion of the protein PlGF in the expression vector pETG (Novagen, Madison, Wis. USA)

A scheme of the subcloning strategy is shown in FIG. 4, wherein the pET3 vector was employed (Novagen Madison Wis.; USA) containing essentially the T7 phage RNA polymerase promoter, the terminator of the same phage, an origin of the replication (ori) and the resistance to ampicillin (amp).

The cDNA insert to be subcloned was obtained through PCR amplification (polymerase chain reaction, ibid. 14.6), generating a cDNA coding for the protein lacking the first 31 amino acids. As template, the Eco R1 DNA fragment, from nucleotide 1 to nucleotide 940, was employed. As primers for RNA polymerase the following oligonucleotides were employed, synthesized with an "Applied Biosystem 381A" oligo-synthesizer:

oligonucleotide A complementary to the coding strand from the nucleotide 768 to the nucleotide 787, in which the GGATCC sequence, Bam H1 recognition site, was inserted between nucelotide 775 and 776, having the following sequence (SEQ ID NO:6):

5'-TCCTCCAAGGGGATCCTGGGTTAC-3'

BamH1 oligonuceotide B complementary to the non-coding strand from nucleotide 404 to nucleotide 421, in which the CATATG sequence, Nde 1 recognition site, was inserted between the nucleotides 414 and 415, having the following sequence (SEQ ID NO:7):

3'-GCAAGGGGTATACTCGTCTGTTCC-5'

Nde1

The nucleotide chain, obtained from PCR, was digested with Nde 1 and Bam H1 and ligated with the prokaryotic pET3 expression vector in the same Nde 1 and Bam H1 sites according to standard protocols. The product was employed for transforming the *E.coli* HB101 strain which had been made competent with the CaCl2 method. The recombinant plasmid was identified and employed for transforming the *E.coli* JM109 strain (DE3, Promega Corporation, Madison Wis., USA).

EXAMPLE 5
Synthesis and isolation of the PIGF protein from bacteria

A single colony was inoculated in L3 broth containing 100 μg/ml of amplicillin (Sigma, St. Louis Mo., USA) and 4 g/l of glucose and then grown at 37° C. to reach an optical density O.D. of 0.35 at 600 nm. IPTG (Sigma) was added to a 1 mM final concentration and the culture was incubated at 37° C. for additional 3 hours. The culture was centrifuged and resuspended in ⅒ of the initial volume of a buffer containing 10 mM Tris-HCl, 1 mM EDTA, pH 8.0 (TE). Following further centrifugation, the precipitate was resuspended in 1/60 of the initial volume into a lysis buffer containing TE, 1% SDS, 0.1M NaCl. Bacteria were divided into aliquots of 500 μl and subjected to lysis by three cycles of freezing and thawing, followed by middle strength sonication.

Figure 5:
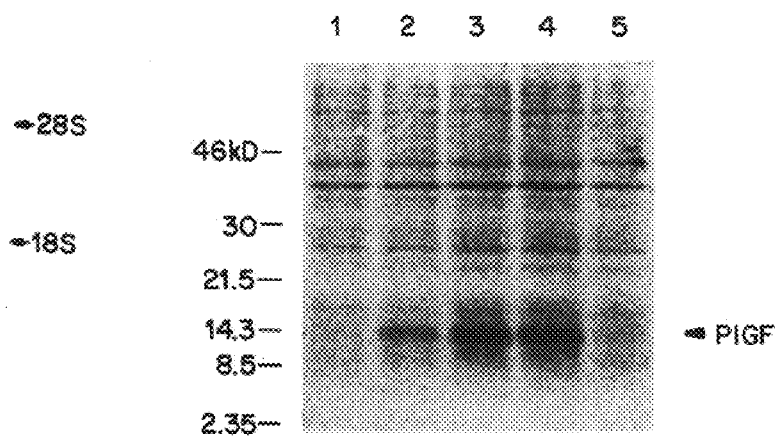
FIG. 5 represents a polyacrylamide gel electrophoresis of the protein PlGF, said protein being obtained through the recombinant way.

An example of the resulting electrophoretic pattern is shown in FIG. 5, wherein lines 1, 2, 3 and 4 represent electrophoretic patterns of proteins from lysates respectively 0, 1, 2 and 3 hours after IPTG induction. As control, line 5 represents the same strain transformed only with the vector lacking the insert, induced with IPTG for 3 hours. Electrophoresis was carried out according to Laemli, Nature 227, 680–685, 1970, in a 15% polyacrylamide gel stained according to the method described by Bradley et al., Anal. Biochem. 182, 157–159 (1989).

EXAMPLE 6

Production of anti PlGF antibodies and immunoprecipitations of PlGF

70 μg of the protein PlGF was employed for immunizing two chickens, as described by Gassmann et al., 1990 Faseb J. 4, 2528–2532. The antibodies so formed were extracted and purified from the yolk through precipitation with polyethylene glycol (PEG) as described by Gassmann et al. (cf. above). The immunoprecipitations were performed by incubating 120–250 μl of cellular lysate, or Cos-1 cell conditioned medium, with 10 or 15 μl or rabbit or chicken antibodies, for 2 hours at room temperature, or 16 hours at 4° C. The immunoreactions with chicken antibodies were further treated with 15 μl of rabbit anti-chicken IgG (SIGMA N. C6778), for 1 hour at room temperature.

The immunocomplex was selected through protein-Sepharose 48 (Pharmacia) and washed twice with 1.2 μl of PBS with 0.01% Nonidet-P40 and 400 μM of NaCl.

The immunoprecipitates were then resuspended and analyzed on polyacrylamide gel under denaturing and reducing conditions according to standard procedure. If COS cells had been previously transfected with the plasmid pSVL-PlGF, a protein of 25 KDa molecular weight is immunoprecipitated, both from the lysate and from the culture medium.

What is claimed:

1. An isolated and purified protein acting as an angiogenic factor comprising the amino acid sequence of SEQ ID NO:2.

* * * * *